US010555887B2

(12) United States Patent
Samain et al.

(10) Patent No.: US 10,555,887 B2
(45) Date of Patent: Feb. 11, 2020

(54) STERILE LIQUID COMPOSITION FOR FILLING WRINKLES

(75) Inventors: Henri Samain, Bievres (FR); Jean-Thierry Simonnet, Cachan (FR)

(73) Assignee: L'OREAL, Paris (FR)

( * ) Notice: Subject to any disclaimer, the term of this patent is extended or adjusted under 35 U.S.C. 154(b) by 131 days.

(21) Appl. No.: 13/996,179

(22) PCT Filed: Dec. 20, 2011

(86) PCT No.: PCT/IB2011/055806
§ 371 (c)(1),
(2), (4) Date: Aug. 14, 2013

(87) PCT Pub. No.: WO2012/085835
PCT Pub. Date: Jun. 28, 2012

(65) Prior Publication Data
US 2013/0317416 A1 Nov. 28, 2013

Related U.S. Application Data

(60) Provisional application No. 61/441,757, filed on Feb. 11, 2011.

(30) Foreign Application Priority Data

Dec. 20, 2010 (FR) ..................... 10 60788

(51) Int. Cl.
*A61K 8/73* (2006.01)
*A61Q 19/08* (2006.01)
*A61K 8/81* (2006.01)
*A61N 5/06* (2006.01)
*A61Q 19/00* (2006.01)

(52) U.S. Cl.
CPC ............... *A61K 8/73* (2013.01); *A61K 8/732* (2013.01); *A61K 8/736* (2013.01); *A61K 8/81* (2013.01); *A61N 5/062* (2013.01); *A61Q 19/00* (2013.01); *A61Q 19/08* (2013.01)

(58) Field of Classification Search
None
See application file for complete search history.

(56) References Cited

U.S. PATENT DOCUMENTS

| 5,254,338 A * | 10/1993 | Sakai ............... A61K 9/0014 424/443 |
| 2006/0239946 A1* | 10/2006 | Samain et al. ............... 424/63 |
| 2007/0212385 A1 | 9/2007 | David |
| 2008/0038306 A1 | 2/2008 | David |
| 2009/0074868 A1 | 3/2009 | Elisseeff et al. |
| 2011/0002997 A1 | 1/2011 | Elisseeff et al. |
| 2011/0087152 A1 | 4/2011 | David et al. |

FOREIGN PATENT DOCUMENTS

| WO | 2007 106457 | 9/2007 |
| WO | 2009 018555 | 2/2009 |
| WO | WO-2011003771 | * 1/2011 |

OTHER PUBLICATIONS

European Pharmacopoeia 5.1 (Parenteral Preparations 2841-2843, 2005).Parenteral Preparations.*
Martens, P. et al., "Characterization of hydrogels formed from acrylate modified poly(vinyl alcohol) macromers", Polymer, vol. 41, No. 21, pp. 7715-7722, ( Oct. 2000) , ( XP 004201762 ).
Nguyen, K. T. et al., "Photopolymerizable hydrogels for tissue engineering applications", Biomaterials, vol. 23, No. 22, pp. 4307-4314, ( Nov. 2002) , ( XP 004374369 ).
Elisseeff, J. et al.,"Transdermal photopolymeriazation for minimally invasive implantation", Proceedings of the National Academy of Sciences, National Academy of Sciences, vol. 96, No. 6, pp. 3104-3107, ( Mar. 1999 ), ( XP-001009855 ).
Ichimura, K. et al., "Preparation and characteristics of photocrosslinkable poly(vinyl alcohol)", Journal of Polymer Science, vol. 20, pp. 1419-1432, (1982 ). ( XP-002658584 ).
French Search Report dated Sep. 9, 2011 in French Patent Application 1060788.
Written Opinion dated Dec. 20, 2010 in French application FR 1060788 (with computer generated translation).
Written Opinion Issued in PCT/IB11/055806 Filed Dec. 20, 2011(with computer generated translation).
International Search Report dated Jun. 8, 2012 in PCT/IB11/055806 Filed Dec. 20, 2011.

* cited by examiner

Primary Examiner — Tigabu Kassa
(74) Attorney, Agent, or Firm — Oblon, McClelland, Maier & Neustadt, L.L.P.

(57) ABSTRACT

The subject matter of the present invention is a sterile liquid composition dedicated to administration into or through the skin and/or the lips, wherein said composition comprises, in a physiologically acceptable medium, at least one photo-crosslinkable compound, wherein said compound comprises at least one activated photo-dimerizable group having at least one activated double bond and selected from photo-dimerizable groups carrying a stilbazolium function of formula (Ia) or (Ib) and wherein the photo-dimerizable groups carry a styrylazolium function of formula (II), the photo-dimerizable group(s) being carried by a partially or totally hydrolysed poly(vinyl acetate) polymer, a polysaccharide or a polyvinyl alcohol.

4 Claims, 3 Drawing Sheets

Figure 1A:
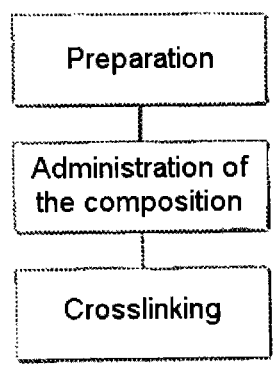

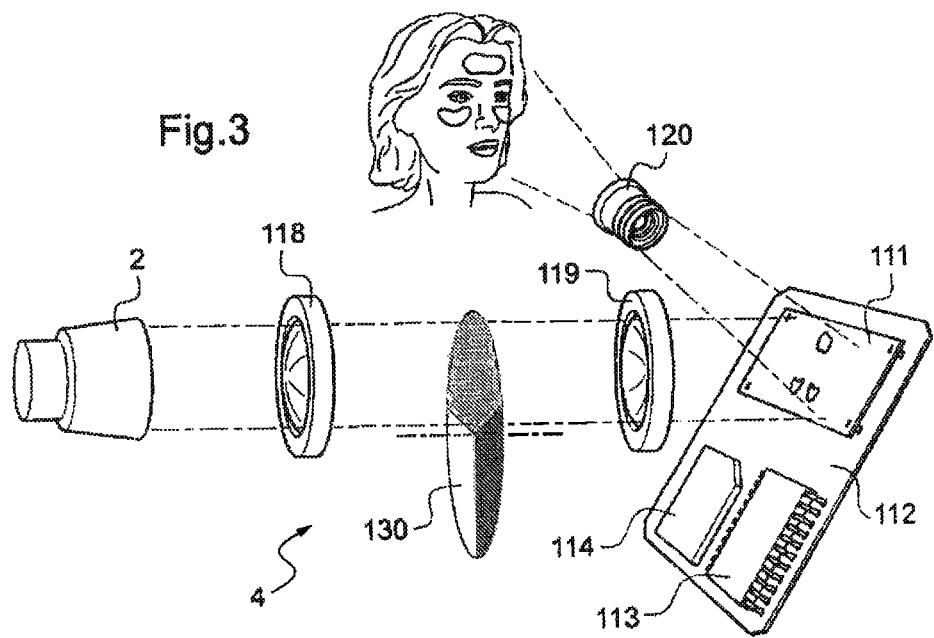
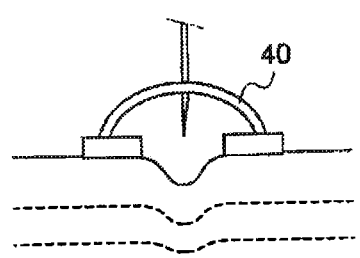 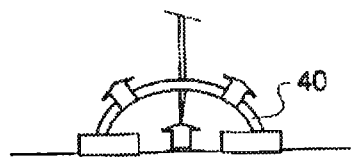

STERILE LIQUID COMPOSITION FOR FILLING WRINKLES

The present invention relates to the treatment of esthetic defects and imperfections of the skin and of the lips.

These imperfections are of various origins and may or may not be due to age.

Thus, imperfections of the skin can result from skin infections, for instance acne scars, or from the effects of a surgical procedure, such as scars.

With regard to age-related imperfections, wrinkles are clearly the most representative thereof.

Among these wrinkles, it is possible to distinguish "marked" wrinkles, which are very visible and which can have a depth of 300 microns or more, "medium" wrinkles, which are visible and which have a depth ranging between 150 microns and 300 microns, and "slight" wrinkles, which are less visible than those above and which have a depth of less than 150 microns.

For obvious reasons, the presence of wrinkles on the face often poses esthetic problems which, depending on the individual, can be difficult to live with, and there is therefore a need for a palliative or palliatives for countering the visibility of the abovementioned imperfections and more particularly wrinkles.

It is known that these imperfections can be corrected by applying to the skin active agents capable of tightening the skin via a fiery tensioning effect, this tension making it possible to smooth out the skin and to immediately reduce the wrinkles and fine lines, or even to cause them to disappear.

However, when applied topically, these active agents penetrate only very slightly, thus exerting only a limited effect over time and in terms of strength. What is more, they are effective only on the surface wrinkles of the skin and are less effective on the deeper wrinkles, for which their action is, on the other hand, weak and not very long-lasting.

Another solution consists in treating the subcutaneous muscles, called skin muscles, for example via a surgical procedure.

Thus, the wrinkles formed around the eyes, the forehead and the mouth can be treated via the corresponding skin muscles. Even though this approach has the advantage of being long-lasting, it has several drawbacks which greatly reduce its development. It is painful, it may be contraindicated and it is relatively expensive. It is also reputed to have the risk of causing unwanted esthetic effects such as, in particular, a lack of natural appearance, or even skin-slackening or local-paralysis effects.

Another treatment alternative aims to treat wrinkles by injection of filling active agents. This technique makes it possible to improve the surface condition by smoothing out the skin and reducing the reliefs thereof. It is also used for increasing the volume of certain parts of the body, for example of the face, in particular for the edge of the lips, but also for repairing deformations due, for example, to an accident.

In this type of injection, molecules such as proteins, in particular collagen, or sugar derivatives, such as hyaluronic acid, are used. These compounds have a sufficient viscosity for conferring on the injection site a volume effect which makes it possible to significantly reduce or even completely modify the visibility of the original depression which was initially present and described as a wrinkle.

Today, the most common injection is carried out with a hyaluronic acid gel used in a crosslinked form, which has proved to be much more effective than non-crosslinked hyaluronic acid. For this, the hyaluronic acid has, at the time of use, a level of crosslinking intended to give it the desired consistency.

However, this technique also has limitations.

In particular, the viscosity inherent in the crosslinking, and necessary for filling the wrinkle, unfortunately generates, upon injection, a painful sensation for the patient.

One alternative would therefore be to carry out the crosslinking and/or polymerization only in situ, and to inject the filling agent in a non-crosslinked form which therefore has a significantly lower viscosity.

However, the use of fluid compounds capable of thickening once injected, via a crosslinking effect, comes up against several problems in many cases. Indeed, generally, crosslinkable chemical polymers require the use of powerful oxidants (peroxides), of a metal catalyst, and/or an elevation of the temperature, in an anhydrous medium, which are conditions that are not very compatible with a biological medium.

Thus, monomers, such as cyanoacrylate derivatives, require, for their polymerization, the presence of additional compounds which are not very compatible with a cutaneous use. Likewise, compounds capable of crosslinking under the effect of light generally require, for their part, photoinitiators which are physiologically incompatible and often involve large amounts of light irradiation, in particular in the ultraviolet range.

By way of illustration of the techniques already proposed and based on in situ polymer crosslinking, mention may in particular be made of the use of a photo-crosslinkable compound for treating the hair (WO 2004/054527) and of injectable compositions comprising a polymerizable hydrogel acrylate monomer and an initiator which may be a photoinitiator, a thermal initiator or a chemical initiator, as proposed in WO 2007/106457, for creating an augmentation of biological tissue.

Photo-dimerizable cinnamic acid derivatives, and in particular photo-crosslinkable derivatives of hyaluronic acid that are functionalized with cinnamic acid derivatives, are also known from EP 0713859. However, the latter are described therein only for the purposes of preparing photo-curable film.

There remains, therefore, a need for new compositions and methods for masking marked reliefs, in particular "marked" wrinkles and "medium" wrinkles, and which completely or partly solve the problems discussed above.

An object of the invention is in particular to provide a composition and a device which make it possible to treat all sorts of wrinkles, ranging from slight wrinkles to marked wrinkles, and also the other reliefs of the skin, such as stretchmarks, scars, folds and dilated pores.

Unexpectedly, the inventors have noted that it proves to be possible to meet this need provided that specific compounds are used.

According to a first aspect, the subject of the invention is a sterile liquid composition dedicated to administration into or through the skin and/or the lips, comprising, in a physiologically acceptable medium, at least one photo-crosslinkable compound, wherein said compound comprises at least one activated photo-dimerizable group having at least one activated double bond and selected from:

a) photo-dimerizable groups bearing a stilbazolium function of formula (Ia) or (Ib):

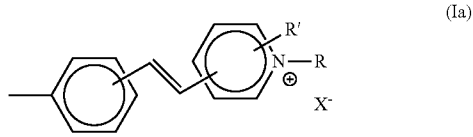

where:
R represents a hydrogen atom or a $C_1$-$C_4$ alkyl or $C_1$-$C_4$ hydroxyalkyl group, R' represents a hydrogen atom or a $C_1$-$C_4$ alkyl group, and
$X^-$ denotes an ion selected from chloride, bromide, iodide, perchlorate, tetrafluoroborate, methyl sulfate, phosphate, sulfate, methanesulfonate and p-toluenesulfonate ions,

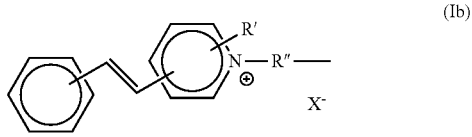

where:
R" denotes a divalent alkylene radical having from 2 to 8 carbon atoms,
R' represents a hydrogen atom or a $C_1$-$C_4$ alkyl group, and
$X^-$ has the same meaning as that described for formula (Ia) above,
b) photo-dimerizable groups bearing a styrylazolium function of formula (II):

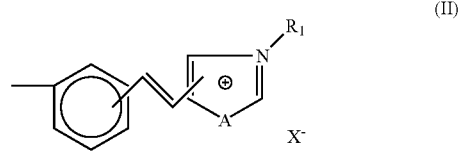

wherein:
$R_1$ denotes a hydrogen atom or a $C_1$-$C_4$ alkyl or $C_1$-$C_4$ hydroxyalkyl group,
A denotes a sulfur atom, an oxygen atom or a group NR' or $C(R')_2$, R', with R' representing a hydrogen atom or a $C_1$-$C_4$ alkyl group, and
$X^-$ has the same meaning as that described for formula (Ia) above, the photo-dimerizable group(s) being borne by a partially or totally hydrolyzed poly(vinyl acetate) polymer, a polysaccharide or a polyvinyl alcohol.

The term "physiologically acceptable medium" is intended to mean a medium devoid of toxicity and compatible with the injection and/or the application of the composition in or through the skin and/or the lips.

The term "sterile" is intended to describe an environment capable of guaranteeing that the compound and/or the composition which contains it has the innocuousness required for administration into or through the skin and/or the lips, in particular intraepidermally and/or intradermally and/or subcutaneously. In particular, it is essential for the composition formed of the physiologically acceptable medium comprising said photo-crosslinkable compound, and which has to be administered according to an injection technique, for example according to the mesotherapy technique, to be devoid of any contaminating substance capable of initiating an adverse side reaction in the host organism.

For the purposes of the present invention, a photo-dimerizable group is a chemical group which results in photo-dimerization reactions under irradiation.

For the purposes of the present invention, the term "photo-dimerization" is intended to mean a chemical reaction between two double bonds (of 2+2 type) or two pairs of double bonds (of 4+4 type) and more preferentially between two double bonds (of 2+2 type).

Thus, the double bond under consideration according to the invention, when it is photo-stimulated or in other words subjected to specific radiation, generally UV radiation, proves to be capable of reacting with another double bond via cyclization.

As detailed hereinafter, the double bonds which interact are ethylene functions, i.e. of $CH_2=CH_2$ type.

For the purposes of the invention, the double bond under consideration is termed activated. This characterization means that the double bond is spontaneously photo-dimerizable in response to a photostimulus, without requiring the obligatory presence of a photoinitiator or of a chemical initiator.

Consequently, a composition according to the invention is advantageously devoid of photoinitiator and/or of chemical initiator.

The activation of the double bond intended to dimerize is commonly induced by the presence, in proximity thereto, generally in the alpha position, of an electron-withdrawing group, such as, for example, an aromatic nucleus like a phenyl.

With regard to the photo-crosslinkable compound, it comprises at least one photo-dimerizable group as previously defined.

The photo-crosslinkable compound derives from the functionalization of a natural backbone, preferably polymer backbone with at least one photo-dimerizable group.

This functionalization falls within the competence of those skilled in the art.

As previously specified, these polymer backbones are selected from natural polymers, such as polysaccharides, and synthetic polymers, such as partially or totally hydrolyzed poly(vinyl acetate) and polyvinyl alcohol (PVA).

The polysaccharides suitable for the invention may in particular be selected from chondroitin sulfate, keratan, keratan sulfate, heparin, heparin sulfate, xanthan, carrageenan, chitosan, cellulose and its derivatives, alginate, starch, dextran, pullulan and galactomannan, and biologically acceptable salts thereof.

According to another aspect of the invention, the subject thereof is a system for treating the skin and/or the lips, comprising:
a packaging containing at least one dose of a composition as defined above, and
a device for injection into or through the skin and/or the lips or a device for microperforation of the skin and/or of the lips, dedicated to the administration of said dose.

For the purposes of the present invention, the term "treatment area" is intended to mean an area of the skin and/or of the lips which has received a part of the composition and/or of the light intended to cause crosslinking.

The expression "injectable composition according to the invention" is intended to mean both the composition claimed for therapeutic use thereof and the composition of a treatment device according to the invention.

Photo-Crosslinkable Compound

According to the invention, a photo-crosslinkable compound comprises at least one photo-dimerizable unit which has a photo-dimerizable activated double bond, borne by a partially or totally hydrolyzed poly(vinyl acetate) polymer, a polysaccharide or a polyvinyl alcohol.

Advantageously, the photo-crosslinkable compound according to the invention may bear one or more function(s) which are cyclizable according to a 2/2 reaction, and which are sensitive to light irradiation, in the absence of photoinitiator and/or of chemical initiator.

A crosslinkable compound according to the invention may be pre-crosslinked.

However, for obvious reasons, this degree of crosslinking is adjusted so as not to confer too high a viscosity on the corresponding gel, which would be liable to generate discomfort or even pain at the moment of administration, and which the present invention is precisely seeking to dispense with.

Photo-Dimerizable Group

For the purposes of the present invention, the term "photo-dimerizable group" is intended to mean a chemical group which results in photo-dimerization reactions under irradiation.

For the purposes of the present invention, the term "photo-dimerization" is intended to mean a chemical reaction between two double bonds (of 2+2 type) or two pairs of double bonds (of 4+4 type).

The case of a reaction between two double bonds can be represented diagrammatically in the following way:

These photo-dimerization reactions are defined in the document Advanced Organic Chemistry, J Marck, 4th edition, Wiley Interscience, NY 1992, p 855.

The materials having photo-dimerizable groups according to the invention have the advantage of being stable with respect to oxygen, moisture and heat, and of resulting in reversible crosslinking.

In addition, the photo-dimerizable groups according to the invention are very photosensitive. Consequently, irradiation, even of low energy, results in rapid and efficient crosslinking of the material, which, in the case of an application in the cosmetics field, leads to a short, low-energy irradiation which does not cause degradation of the skin and/or of the lips.

The photo-dimerizable groups that may be used according to the invention are selected from:

a) photo-dimerizable groups bearing a stilbazolium function of formula (Ia) or (Ib):

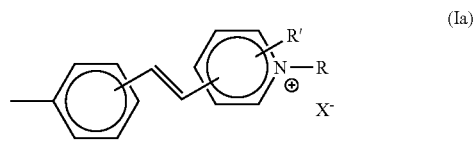

where:
R represents a hydrogen atom or a $C_1$-$C_4$ alkyl or $C_1$-$C_4$ hydroxyalkyl group, preferably R represents a hydrogen atom, a methyl group, an ethyl group or a hydroxyethyl group, preferentially R is a methyl group;

R' represents a hydrogen atom or a $C_1$-$C_4$ alkyl group, preferably R' represents a hydrogen atom; and $X^-$ denotes an ion selected from chloride, bromide, iodide, perchlorate, tetrafluoroborate, methyl sulfate, phosphate, sulfate, methanesulfonate and p-toluenesulfonate ions, preferably $X^-$ is an ion selected from chloride and methyl sulphate ions, preferentially $X^-$ is the methyl sulfate ion,

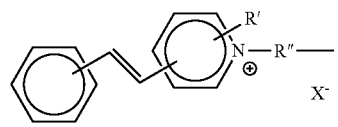

where:
R" denotes an alkylene (divalent) radical having from 2 to 8 carbon atoms, preferably R" denotes an alkylene (divalent) radical having from 2 to 4 carbon atoms;

R' represents a hydrogen atom or a $C_1$-$C_4$ alkyl group, with preferably R' representing a hydrogen atom; and $X^-$ has the same meaning as that described for formula (Ia) above, b) photo-dimerizable groups bearing a styrylazolium function of formula (II):

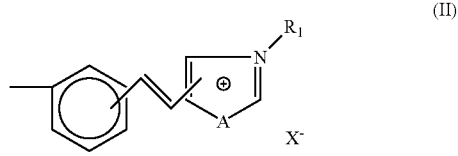

wherein:
$R_1$ denotes a hydrogen atom or a $C_1$-$C_4$ alkyl or $C_1$-$C_4$ hydroxyalkyl group;

A denotes a sulfur atom, an oxygen atom or a group NR' or C(R')$_2$, R', with R' representing a hydrogen atom or a $C_1$-$C_4$ alkyl group, R' preferably representing a hydrogen atom; and $X^-$ has the same meaning as that described for formula (Ia) above.

Such chemical groups have activated double bonds, such that the photo-dimerization of these double bonds is spontaneously triggered in the UVA range, without requiring a photoinitiator.

According to one preferred embodiment, the photo-dimerizable groups that may be used according to the invention bear a stilbazolium function of formula (Ia):

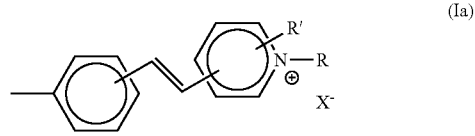

where:
R represents a hydrogen atom or a $C_1$-$C_4$ alkyl or $C_1$-$C_4$ hydroxyalkyl group, R' represents a hydrogen atom or a $C_1$-$C_4$ alkyl group, and $X^-$ denotes an ion selected from chloride, bromide, iodide, perchlorate, tetrafluoroborate, methyl sulfate, phosphate, sulfate, methanesulfonate and p-toluenesulfonate ions.

With regard to the compounds having photo-dimerizable groups bearing a stylbazolium function, they are obtained by reacting the polymer under consideration with a chemical entity comprising a group of formula (Ia) or (Ib).

Preferably, the chemical entity comprising a group (Ia) bears a reactive group W of aldehyde or acetal type.

In other words, this chemical entity corresponds to the general formula W-A, with A denoting the group (Ia).

As chemical entities which can be used for grafting groups of styrylpyridinium type, mention may in particular be made of the quaternary salts of 2-(4-formylstyryl)pyridinium, 4-(4-formyl styryl)pyridinium, 2-(3-formylstyryl)pyridinium, N-methyl-2-(4-formylstyryl)pyridinium, N-methyl-3-(4-formylstyryl)pyridinium, N-methyl-2-(3-formylstyryl)pyridinium, N-methyl-2-(2-formylstyryl)pyridinium, N-ethyl-2-(4-formylstyryl)pyridinium, N-(2-hydroxyethyl)-2-(4-formylstyryl)pyridinium, N-(2-hydroxyethyl)-4-(4-formylstyryl)pyridinium, N-methyl-4-(4-formylstyryl)pyridinium, N-methyl-4-(3-formylstyryl)pyridinium.

The quaternary pyridinium salts may be chloride, bromide, iodide, perchlorate, tetrafluoroborate, methosulfate, phosphate, sulfate, methanesulfonate or p-toluenesulfonate salts. Such chemical entities are described in GB-A-2030575.

As an example of entities, mention may be made of 4-(4-formylphenylethenyl)-1-methylpyridinium methosulfate, 1-(3-ethoxycarbonylmethyl)-4-[2-(4-formylphenyl)ethenyl]pyridinium bromide and 1-(methoxycarbonylpropyl)-4-[2-(4-formylphenyl)ethenyl]pyridinium bromide. Such entities are described in US 2007/0112094.

Preferably, N-methyl-4-(4-formylstyryl)pyridinium methyl sulfate (RN=74401-04-0), in particular sold by the company Wako, is used.

Advantageously, the chemical entities of formula W-A react with a polymer of polyvinyl alcohol or polyvinyl acetal type as described in the documents previously mentioned.

For example, a polyvinyl alcohol grafted polymer comprising units having the following structure is thus obtained:

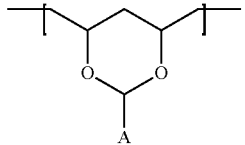

A

Polyvinyl alcohol polymers grafted with styrylpyridinium groups are in particular described in the publication Ichimura K et al, Preparation and Characteristics of photo-crosslinkable poly(vinyl alcohol), Journal of polymer science, polymer chemistry edition, Vol 20, 1419-1432 (1982).

The polymers can be obtained by reacting polyvinyl alcohol or partially hydrolyzed poly(vinyl acetate) with styrylpyridinium salts comprising a formyl or acetal group, as described in GB-A-2030575, WO 96/29312, U.S. Pat. No. 5,061,603, GB-A-2076826 and EP-A-092901.

Cellulose polymers grafted with styrylpyridinium groups are in particular described in US 2007/0112094.

Preferably, the chemical entity comprising a group (Ia) bears a reactive group which is a chlorine atom.

In this variant, the chemical entity corresponds to a general formula Cl-A', with A' denoting the group (Ia).

As chemical entity of Cl-A' type, use is preferably made of the one of formula:

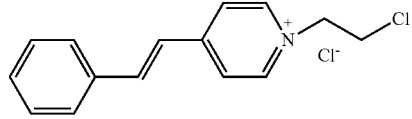

corresponding to the chlorinated compound (I) described in the preparation examples hereinafter.

Advantageously, the photo-crosslinkable compound comprising the groups (Ib) is advantageously obtained by reacting the entity Cl-A' with the polysaccharide selected from those previously defined, in the presence of water.

For their part, the compounds having photo-dimerizable groups bearing a styrylazolium function are obtained by reacting the polymer with a chemical entity comprising a group of formula (II).

Preferably, the chemical entity comprising a group (II) bears a reactive group W of aldehyde or acetal type.

In other words, the chemical entity corresponds to a general formula W-B, with B denoting the group (II).

As chemical entities which can be used for grafting styrylazolium groups, mention may be made of those described in EP-A-313220.

Advantageously, these chemical entities of formula W-B react with a polymer of polyvinyl alcohol or polyvinyl acetal type as described in the documents previously mentioned.

A polyvinyl alcohol grafted polymer comprising units having the following structure is thus obtained:

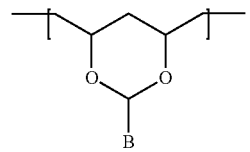

B

Polyvinyl alcohol polymers grafted with styrylazolium groups are in particular described in EP-A-313220. In that document, these polymers can be obtained by reacting polyvinyl alcohol or partially hydrolyzed poly(vinyl acetate) with styrylazolium salts comprising an aldehyde or acetal group.

Advantageously, in the compositions of the invention, the compound comprising at least one photo-dimerizable group is a hydrocarbon-based polymer selected from polyvinyl alcohol, totally or partially hydrolyzed poly(vinyl acetate) and polysaccharides selected from chondroitin sulfate, keratan, keratan sulfate, heparin, heparin sulfate, xanthan, carrageenan, chitosan, cellulose and its derivatives, alginate, starch, dextran, pullulan and galactomannan, and biologically acceptable salts thereof.

Even more advantageously, it is in the form of particles, in particular of dispersed particles.

Thus, in the latter case, polymer particles are very preferentially polyvinyl alcohol particles.

Thus, according to one embodiment variant, the photo-crosslinkable compound is a polyvinyl alcohol (PVA) partly functionalized with one or more hydroxyl function(s) and one or more function(s) of formula (III):

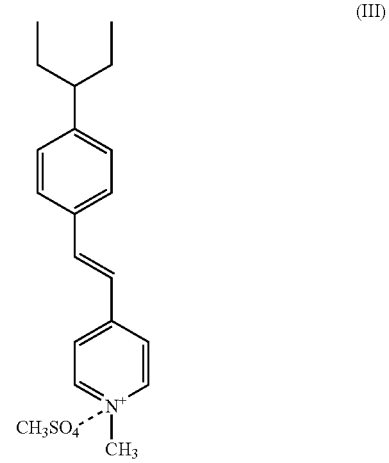

The degree of polymerization of the polyvinyl alcohol may be between 100 and 5000.

Advantageously, the polymer has a degree of substitution, as % of functions of formula (Ia), (Ib) or (II) as defined above, which can be between 0.1 and 25.

The following scheme represents a variant where the polymer is PVA-SbQ (polyvinyl alcohol PVA polymer bearing some hydrolyzed functions and some functions grafted with stilbazolium entities), which is capable of crosslinking under the effect of light, as illustrated hereinafter.

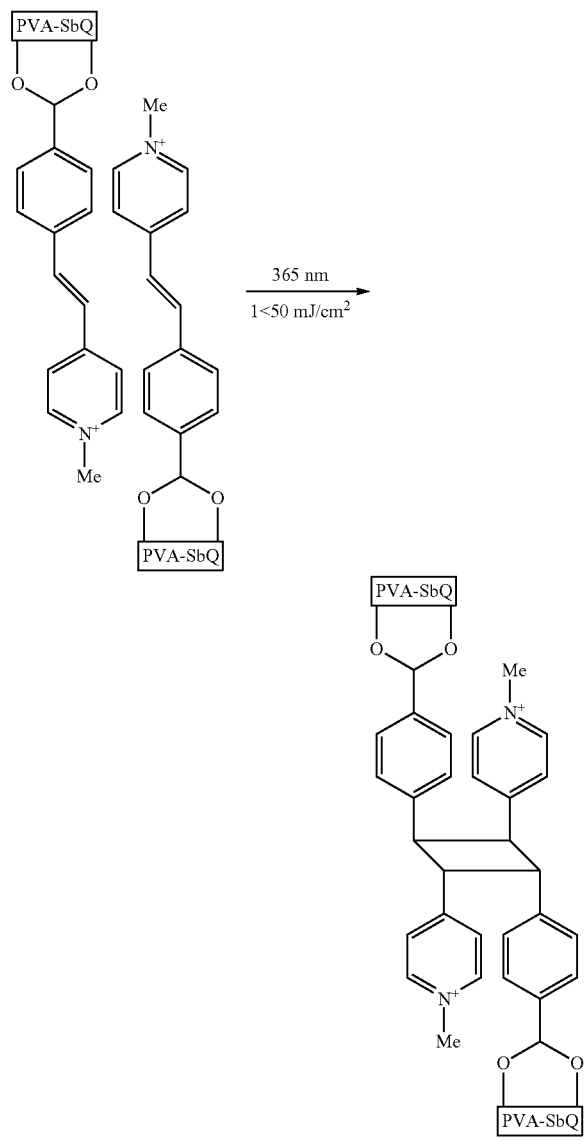 [SMILES: COC(OC)c1ccc(/C=C/c2cc[n+](C)cc2)cc1 ; COC(OC)c1ccc(/C=C/c2cc[n+](C)cc2)cc1 ; COC(OC)c1ccc(C2C(c3cc[n+](C)cc3)C(c3ccc(C(OC)OC)cc3)C2c2cc[n+](C)cc2)cc1]

These materials are particularly appreciated since they do not require a photoinitiator and react to visible light or to radiation which may comprise both UV light and visible light, in particular a low dose of UV.

It should be noted that the choice of UV and/or visible light is generally adjusted while taking into consideration the depth at which a composition according to the invention is injected in the epidermis to be treated.

Thus, if the composition is injected above 1000 µm, materials which react to radiation comprising visible light, in particular between 500 nm and 1000 nm, are preferred.

If the composition is injected between 300 and 1000 µm, materials which react to radiation comprising visible light, in particular between 450 nm and 650 nm, or comprising both UV light and visible light, are, on the other hand, preferred.

Finally, if the composition is injected between 0 and 300 µm, materials which react to radiation comprising UV light or comprising both UV light and visible light in a ratio of 50% in the 350-400 nm region and 50% in the 400-500 nm region, or to visible light, are preferred.

The invention is also directed toward, as functionalized polymer, aqueous dispersions of a polymer of partially saponified (hydrolyzed) poly(vinyl acetate) type bearing stilbazolium groups, placed in the presence of, in particular mixed with, poly(vinyl acetate) particles.

According to another embodiment variant, the photo-crosslinkable compound is represented by a polysaccharide which is functionalized with photo-dimerizable groups.

It may in particular be a polysaccharide which can in particular be selected from chondroitin sulfate, keratan, keratan sulfate, heparin, heparin sulfate, xanthan, carrageenan, chitosan, cellulose and its derivatives, alginate, starch, dextran, pullulan and galactomannan, and biologically acceptable salts thereof.

The degree of functionalization is of course adjusted so as to be able to confer the degree of crosslinking required during the in situ activation.

According to the invention, the degree of functionalization with photo-dimerizable units is at least 0.1%, or even at least 0.5%, or even at least 2%.

As previously specified, in a composition according to the invention, the photo-dimerizable groups are borne by a poly(vinyl acetate) polymer, a polyvinyl alcohol or a polysaccharide.

Preferably, in a composition according to the invention, the photo-dimerizable groups are borne by a polyvinyl alcohol.

The crosslinkable compound may be carried in a physiologically acceptable medium and in particular an aqueous medium or even pure water.

The presence of water does not prevent it from photo-crosslinking, thereby presenting the advantage of making it possible to perform photo-crosslinking in situ.

According to the invention, the photo-crosslinkable compound has a number-average molecular weight ranging from 2000 to 100 000 and preferably ranging from 2000 to 20 000.

Photo-Dimerization

The composition may contain a single polymer bearing functions which may or may not be of different nature.

A mixture of polymers having different functions may also be used.

Consequently, the reactions can be carried out between two photo-dimerizable groups which may or may not be of the same chemical nature.

The activated double bonds may react on another double bond of the same chemical nature or may react with another double bond of different chemical nature.

The photo-dimerization protocol is described in greater detail hereinafter.

The crosslinkable compound may be soluble or dispersed in the composition used for its administration.

Injectable Sterile Liquid Composition

The composition may or may not be cosmetic.

As previously specified, the compositions under consideration according to the invention must be administered in a form devoid of viable or revivable, potentially infectious, microorganisms known to those skilled in the art. In order to meet this requirement, the physiologically acceptable liquid medium and the photo-crosslinkable compound forming the administerable composition according to the invention can be subjected, together or separately, to a sterilization process according to one of the conventional methods well known to those skilled in the art, such as, for example, autoclave heating, or ionizing irradiation, such as electron beams and gamma rays.

The composition may comprise a physiologically acceptable aqueous or nonaqueous medium.

The composition may comprise a physiologically acceptable solvent or a mixture of physiologically acceptable solvents.

By way of aqueous or nonaqueous medium suitable for the invention, mention may, for example, be made of water, alcohols, polyols, polyol ethers, and mixtures thereof. By way of isotonic agents suitable for the preparation of a composition suitable for the invention, mention may be made of sugars and sodium chloride.

The alcohols may be selected from $C_1$-$C_6$ lower alkanols, and preferably selected from ethanol, propanol and isopropanol.

The polyols may be selected from glycerol, propylene glycol, polyethylene glycol, hexylene glycol, glycerol and pentanediol.

These polyols will have the effect of plasticizing the crosslinked polymer and of modifying its final mechanical properties. The polymer/polyol ratio ranges from 100/0 to 1/10.

Thus, a composition according to the invention is generally used in the form of an aqueous or nonaqueous, sterile isotonic solution, in the form of a dispersion, a suspension or an emulsion.

The aqueous or nonaqueous medium may represent from 0.1% to 99% by weight relative to the total weight of the composition, preferably from 30% to 99% by weight or even from 50% to 99% by weight.

The photo-crosslinkable compound may represent at least 2%, or even at least 5%, or even 10% of the total volume of the composition.

The photo-crosslinkable compound may be present in the composition in a content ranging from 1% to 15% by weight, relative to the total weight of the composition, and preferably from 5% to 10% by weight.

For obvious reasons, the composition is sufficiently fluid to facilitate injection with a moderate pressure.

The composition has, for example, at the time of injection, a viscosity of less than 100 000 cps, and preferably less than 10 000 cps, measured at T=20° C., in CPS.

A composition according to the invention may comprise, in addition to the photo-crosslinkable compound, any excipient normally used in the field of injectable sterile solutions.

Advantageously, a composition according to the invention is devoid of photoinitiator.

By representative way of conventional photoinitiators which are therefore not required according to the invention, mention may in particular be made of thioxanthone, rose Bengal, phloxine, eosin, erythrosine, fluorescein, acriflavine, thionine, riboflavin, proflavine, chlorophylls, hematoporphyrin, methylene blue, and mixtures thereof, this list not being limiting.

On the other hand, a composition according to the invention may advantageously comprise an optical tracer or a fluorescent compound.

Optical Tracer/Fluorescent Compound

Such a compound is advantageous insofar as it can enable the practitioner carrying out the injection of the photo-crosslinkable compound under consideration according to the invention to effectively control the localization of the compound injected and/or the dose of compound administered.

This option allows said practitioner to more easily irradiate the entire area where the composition is located.

The term "optical tracer" is intended to mean a compound which changes color or becomes colorless at the time of illumination, i.e. when the polymerization takes place, for example a "fluorescent" compound which absorbs light from the ultraviolet spectrum and optionally visible light, and which converts the absorbed energy into fluorescent light of longer wavelengths, emitted in the ultraviolet or visible part of the spectrum.

It may be a question of optical brighteners, which may be transparent and colorless, which do not absorb in the visible light range, but only in the UV range and which convert the absorbed energy into fluorescent light of longer wavelength, for example longer by 20 nm, better still 50 nm or even 100 nm, emitted in the visible part of the spectrum.

The impression of color generated by these brighteners can therefore only be created by predominantly blue, purely fluorescent light having wavelengths ranging from 400 to 500 nm.

These compounds may be in solution or particulate.

The fluorescent compound may be a diketopyrrolopyrrole of formula:

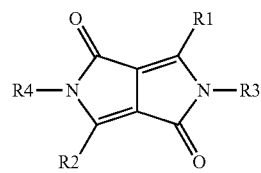

wherein $R_1$, $R_2$, $R_3$ and $R_4$, independently of one another, represent a hydrogen atom; a halogen atom; a $C_6$-$C_{30}$ aryl group; a hydroxyl group; a cyano group; a nitro group; a sulfo group; an amino group; an acylamino group; a di($C_1$-$C_6$)alkylamino group; a dihydroxy($C_1$-$C_6$)alkylamino group; a ($C_1$-$C_6$)alkylhydroxy($C_1$-$C_6$)alkylamino group; a ($C_1$-$C_6$)alcoxy group; a ($C_1$-$C_6$)alcoxycarbonyl group; a $C_1$-$C_6$ carboxyalcoxy group; a piperidinosulfonyl group; a pyrrolidino group; a ($C_1$-$C_6$)alkylhalo($C_1$-$C_6$)alkylamino group; a benzoyl($C_1$-$C_6$)alkyle group; a vinyl group; a formyl group; a $C_6$-$C_{30}$ aryl radical optionally substituted with one or more groups selected from the following groups: hydroxyl, linear, branched or cyclic $C_1$-$C_6$ alcoxy, linear, branched or cyclic alkyl comprising from 1 to 22 carbon atoms, itself optionally substituted with one or more hydroxyl, amino or $C_1$-$C_6$ alcoxy groups, a linear, branched or cyclic alkyl radical comprising from 1 to 22 carbon atoms, optionally substituted with one or more groups selected from hydroxyl, amino, linear, branched or cyclic $C_1$-$C_6$ alcoxy, optionally substituted aryl, carboxyl and sulfo groups, and a halogen atom, it being possible for this alkyl radical to be interrupted with a heteroatom.

The fluorescent compound may be a naphthalimide of formula:

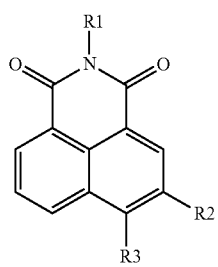

where:

R$_1$, R$_2$ and R$_3$, independently of one another, represent a hydrogen atom; a halogen atom; a C$_6$-C$_{30}$ aryl group; a hydroxyl group; a cyano group; a nitro group; a sulfo group; an amino group; an acylamino group; a di(C$_1$-C$_6$)alkylamino group; a dihydroxy(C$_1$-C$_6$)alkylamino group; a (C$_1$-C$_6$)alkylhydroxy(C$_1$-C$_6$)alkylamino group; a (C$_1$-C$_6$)alcoxy group; a (C$_1$-C$_6$)alcoxycarbonyl group; a C$_1$-C$_6$ carboxyalcoxy group; a piperidinosulfonyl group; a pyrrolidino group; a (C$_1$-C$_6$)alkylhalo(C$_1$-C$_6$)alkylamino group; a benzoyl(C$_1$-C$_6$)alkyle group; a vinyl group; a formyl group; a C$_6$-C$_{30}$ aryl radical optionally substituted with one or more groups selected from the following groups: hydroxyl, linear, branched or cyclic C$_1$-C$_6$ alcoxy, linear, branched or cyclic alkyl comprising from 1 to 22 carbon atoms, itself being optionally substituted with one or more hydroxyl, amino or C$_1$-C$_6$ alcoxy groups, a linear, branched or cyclic alkyl radical comprising from 1 to 22 carbon atoms, optionally substituted with one or more groups selected from hydroxyl, amino, linear, branched or cyclic C$_1$-C$_6$ alcoxy, optionally substituted aryl, carboxyl and sulfo groups, and a halogen atom, it being possible for this alkyl radical to be interrupted with a heteroatom; the substituents R$_1$, R$_2$ and R$_3$ can form, with the carbon atoms to which they are attached, an aromatic or nonaromatic C$_6$-C$_{30}$ ring or a heterocyclic ring comprising in total from 5 to 30 ring members and from 1 to 5 heteroatoms; these rings being optionally condensed, optionally inserting a carbonyl group, and being optionally substituted with one or more groups selected from C$_1$-C$_4$ alkyl, (C$_1$-C$_4$)alcoxy(C$_1$-C$_4$)alkyl, amino, di(C$_1$-C$_4$)alkylamino, halogen, phenyl, carboxy and tri(C$_1$-C$_4$)alkylammonio(C$_1$-C$_4$)alkyl groups.

The fluorescent compound may be a stilbene derivative, for example of formula:

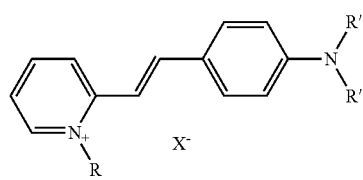

wherein:
R represents a methyl or ethyl radical;
R' represents a methyl radical, and
X$^-$ represents an anion of the chloride, iodide, sulfate, methosulfate, acetate or perchlorate type.

By way of example of a compound of this type, mention may be made of the Photosensitiving Dye NK-557 sold by the company Ubichem, for which R represents an ethyl radical, R' represents a methyl radical and X$^-$ represents an iodide.

The fluorescent compound may be a methyne derivative such as:

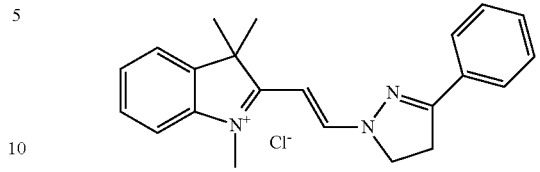

or an oxazine or thiazine derivative of general formula:

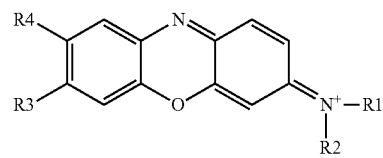

Mention may also be made of dicyanopyrazine derivatives (from the company Nippon Paint), naphtholactam derivatives, azalactone derivatives, rhodamines and xanthene derivatives.

Use may also be made of inorganic pigments or particles (MgO, TiO$_2$, ZnO, Ca(OH)$_2$, etc.) or organic pigments or particles (latex, etc.) comprising such compounds in their core or on their surface.

The fluorescent compound may also be a semiconductor compound which, for example in the form of small particles, called quantum dots, has a fluorescent effect.

Quantum dots are luminescent semiconductor nanoparticles capable of emitting, under light excitation, radiation exhibiting a wavelength of between 400 nm and 700 nm. These nanoparticles can be manufactured according to the processes described, for example, in U.S. Pat. No. 6,225,198 or 5,990,479, in the publications which are cited therein and in the following publications: Dabboussi B. O. et al. "(CdSe)ZnS core-shell quantum dots: synthesis and characterisation of a size series of highly luminescent nanocristallites" Journal of physical chemistry B, vol 101, 1997, pp 9463-9475 and Peng, Xiaogang et al., "Epitaxial Growth of highly Luminescent CdSe/CdS core/shell nanocrystals with photostability and electronic accessibility" Journal of the American Chemical Society, vol 119, No. 30, pp 7019-7029.

Preferred fluorescent compounds are those which emit the colors blue, green or red.

Preferably, the fluorescent compound(s) used as optical agents in the invention are selected from stilbene compounds.

Active Agents

The composition may comprise at least one or more additional active agents.

The cosmetic active agent(s) according to the invention may be seleted from:
anti-aging/antiwrinkle agents,
moisturizing agents,
free-radical scavengers,
agents acting on the microcirculation,
agents acting on the energy metabolism of cells,
hyaluronic acid,
anti-glycation agents,
NO-synthase inhibitors, agents which stimulate the synthesis of dermal or epidermal macromolecules and/or which prevent their degradation,
agents which stimulate fibroblast and/or keratinocyte proliferation,
muscle relaxants,
saccharides,
oligosaccharides, polysaccharides which are optionally hydrolyzed and optionally modified,
amino acids, oligopeptides, peptides, proteins which are optionally hydrolyzed and optionally modified, polyamino acids, enzymes,
animal, vegetable or mineral waxes,
ceramides and pseudoceramides,
hydroxylated organic acids,
antioxidants and free-radical scavengers,
soothing agents,
soluble or dispersed anionic polymers,
soluble or dispersed nonionic polymers,
particles, and
mixtures thereof.

Among the anti-aging additional compounds, mention may most particularly be made of vitamins, such as vitamin A, vitamin C, biotin, B vitamins, such as folic acid, panthenol, niacinamide, fruit acids, α-hydroxy acids, dehydroepiandrosterone (DHEA), micronutrients, phosphatidylcholine, and tensioning agents such as 2-(dimethylamino) ethanol, procaine or 2-(diethylamino)ethyl-4-aminobenzoate.

Advantageously, the injectable composition according to the invention may also contain at least one additional active agent and in particular an antiwrinkle active agent.

Examples of antiwrinkle active agents that may be used according to the invention are ascorbic acid and derivatives thereof, such as magnesium ascorbyl phosphate and ascorbyl glucoside; adenosine and derivatives thereof, in particular nonphosphated derivatives thereof; tocopherol and derivatives thereof, such as tocopheryl acetate; nicotinic acid and precursors thereof, such as nicotinamide; ubiquinone; glutathione and precursors thereof, such as L-2-oxothiazolidine-4-carboxylic acid; C-glycoside compounds and derivatives thereof, in particular those described in application WO 02/051828; plant extracts and especially extracts of sea fennel and of olive leaf, and also plant proteins and hydrolysates thereof, such as rice or soybean protein hydrolysates; algal extracts and in particular laminaria extracts; bacterial extracts; sapogenins, such as diosgenin and extracts of Dioscorea plants, in particular of wild yam, containing the same; α-hydroxy acids; β-hydroxy acids such as salicylic acid and 5-n-octanoylsalicylic acid; oligopeptides and pseudodipeptides and acyl derivatives thereof, in particular {2-[acetyl-(3-trifluoromethylphenyl) amino]-3-methylbutyrylamino}acetic acid and the lipopeptides sold by the company Sederma under the trade names Matrixyl 500 and Matrixyl 3000; lycopene; rhamnose; manganese and magnesium salts, in particular the gluconates; and mixtures thereof. Mention may also be made of vitamins, such as, for example, vitamins B3 or PP, B5, E and K1.

According to one particular embodiment, this or these additional compound(s) is (are) selected from micronutrients, vitamins, in particular vitamin B derivatives, such as panthenol, niacinamide or folic acid, biotin and in particular hyaluronic acid or one of its non-crosslinked or weakly crosslinked derivatives.

The composition may also comprise biological active agents, such as botox, collagen, hyaluronic acid and anti-inflammatories.

The composition may comprise stem cells.

The presence of a biological active agent in the composition may make it possible to limit the diffusion of the composition and to facilitate the resorption of the excess composition.

The amount of active agents depends of course on the nature of the active agent and on the desired effect, but said active agent generally represents from 0.01% to 10%, even from 0.1% to 5%, or even from 0.001% to 30% of the total weight of the composition.

Fibers

The injectable composition according to the invention may also contain fibers.

These fibers, via entanglement, provide the filling material with good cohesion.

The term "fiber" should be understood as meaning an object of length L and of diameter D such that L is greater than D and preferably very much greater than D, D being the diameter of the circle in which the cross section of the fiber is inscribed. In particular, the ratio L/D (or aspect ratio) is chosen in the range from 3.5 to 2500, preferably from 5 to 500 and better still from 5 to 150.

The fibers that can be used in a composition of the invention can be fibers of synthetic or natural and inorganic or organic origin, and they can be flexible or stiff.

They can be short or long, and individual or organized, for example braided.

They may have any shape and may in particular have a circular or polygonal (square, hexagonal or octagonal) cross section depending on the specific application envisioned.

Preferably, the fibers that can be used in a composition according to the invention are selected from natural fibers or derived fibers, such as rayon.

The composition may comprise between 1% and 40% by weight of fibers relative to the total weight of said composition.

Fillers

The distinct fillers of the abovementioned fibers, which may be present in a composition according to the invention, may be of any shape, platelet, spherical, hemispherical or oblong, regardless of the crystallographic form (for example, sheet, cubic, hexagonal, orthorhombic, etc.).

By way of illustration of these fillers, mention may be made of talc, mica, silica, kaolin, poly-β-alanine and polyethylene powders, tetrafluoroethylene (Teflon®) polymer powders, lauroyllysine, starch, boron nitride, polymeric hollow microspheres such as those of polyvinylidene chloride/acrylonitrile, for instance Expancel® (Nobel Industrie), or of acrylic acid copolymers, silicone resin microbeads (Tospearls® from Toshiba, for example), polyorganosiloxane elastomer particles, precipitated calcium carbonate, magnesium carbonate, magnesium hydrogen carbonate, hydroxyapatite, barium sulfate, the aluminum oxides, polyurethane powders, composite fillers, hollow silica microspheres, and glass or ceramic microcapsules. Use may also be made of particles which have the shape of portions of hollow spheres, as described in patent applications JP-2003 128 788 and JP-2000 191 789.

Administration of the Composition

The composition may be injected using any of the modes known to those skilled in the art.

The system may comprise an injection device suitable for intraepidermal and/or intradermal and/or subcutaneous injection.

In one particular example, the injection can be carried out under the nail.

The injection device may be selected from a syringe, a set of microsyringes, a hydraulic laser device or a scalpel.

In one embodiment variant, the injection device may be suitable for the mesotherapy technique.

Mesotherapy is a technique for treatment by intraepidermal and/or intradermal and/or subcutaneous injection of an active product or active products.

The composition is administered according to this technique via injection in the form of multiple small droplets into the epidermis, the dermal-epidermal junction and/or the dermis in order in particular to perform subcutaneous layering. The mesotherapy technique is in particular described in the book "Traité de mésothérapie" ["Treatise on mesotherapy"] by Jacques Le Coz, published by Masson, 2004.

Mesotherapy performed on the face is also known as mesolift or also mesoglow.

Alternatively, the treatment system may comprise a microperforation system with which it is possible to make microholes in the skin and/or the lips, and then to apply the composition topically so that it diffuses naturally into the skin and/or the lips.

The administration by intraepidermal and/or intradermal and/or subcutaneous injection according to the invention aims to inject a composition of the invention into an epidermal, dermal-epidermal and/or dermal region.

The treatment system according to the invention may comprise any injection means suitable for intraepidermal and/or intradermal and/or subcutaneous injection.

Thus, the injection can be performed through a needle normally used for carrying out an intraepidermal and/or intradermal and/or subcutaneous injection, for example suitable for mesotherapy.

A needle of a system according to the invention may have a diameter ranging from 0.26 to 0.4 mm and a length ranging from 4 to 13 mm.

In particular, the needle suitable for the invention may have a diameter of 0.3 mm and a length of 6 mm.

The needle is advantageously disposable.

Advantageously, the needle is associated with a syringe or any other device for delivering said injectable composition through the needle. According to one embodiment variant, a catheter may be inserted between the needle and syringe.

In a known manner, the syringe may be operated manually by the practitioner, or else by means of a syringe support, such as syringe guns.

A hydropneumatic-compression injection gun with a high injection frequency may be used.

Thus, an injection gun suitable for the invention may be, for example, as described in patents EP 1 208 858 or U.S. Pat. No. 5,300,029, incorporated herein by way of reference.

For example, an injection gun suitable for the invention may be the MesoMega®, the Inderm PSI®, the Pistor 4®, the DHN3® or the Rofil Meso Gun U225® sold by the company Rofil (Biophymed).

Depending on the injection device used, the composition according to the invention may be injected in the form of droplets.

Advantageously, the droplets can have an average volume ranging from 0.01 to 0.2 ml and in particular from 0.05 to 0.15 ml.

The treatment system may comprise an injection gun, in particular a hydropneumatic-compression injection gun with a high injection frequency.

According to another aspect of the invention, the subject thereof is an assembly for treating esthetic imperfections of the skin and/or of the lips, comprising:
  i. a treatment system as previously described,
  ii. a lighting system capable of photo-crosslinking the compound.

According to yet another aspect of the invention, the subject thereof is an assembly for treating esthetic imperfections of the skin and/or of the lips, also comprising at least:
  i. one system for analyzing at least one area to be treated,
  ii. one source of other means of activation selected from a source of heat, of microwaves, of sound waves, a light source which does not facilitate crosslinking of the compound(s),
  iii. one system for applying a stress before or during the illumination,
  iv. one device for eliminating the unreacted compounds.

Illumination for Crosslinking

The crosslinking can be carried out in ambient light or else preferably with an artificial light, such as lighting with a lamp, a flash, a laser, or LEDs, for example in the form of an LED matrix.

The injection followed by the illumination makes it possible to produce a resistant material in the skin and/or the lips, thus making it possible to reduce the hollows or to give greater volume.

The lighting system can be arranged so as to illuminate the treatment area externally, through the skin and/or the lips. In one variant, the light may be brought into or under the skin and/or the lips.

The treatment assembly may comprise an optical fiber for lighting the area to be treated internally.

The treatment assembly may comprise a light source with radiation in the visible range and/or radiation in the UV range, and preferably radiation in the visible range (white light).

The light emitted may or may not be monochromatic. The wavelength of the light emitted is preferably centered around 365 nm, in particular between 400 nm and 700 nm, and better still between 365 nm and 550 nm.

The crosslinking can be initiated by the illumination without requiring a photoinitiator.

The crosslinking can be carried out with a low light intensity; the lighting system can produce, for example, a light intensity of less than 50 mJ/$cm^2$ or even than 10 J/$cm^2$.

The lighting system preferably has a light intensity of between 1 mW and 10 W, the exposure times being adapted accordingly.

In particular, the light energy in the UV range is preferably less than 10 J/$cm^2$.

The double feature of the absence of photoinitiator and of a relatively low light intensity is particularly advantageous since it makes it possible to limit the harmful effects of aggressive initiators or prolonged exposure to an intense light, in particular in the UV wavelengths.

The illumination may be overall or localized or even be structured and represent an image.

The structuring may be carried out so as to treat certain particular areas, for instance the bottom of the wrinkles, the edge of the lips, the hollows (acne scars, pores, stretchmarks, etc.).

Several structuring approaches are possible from a technical point of view: illuminating the surface with a projected "image" or illuminating the surface with a mobile ray, for example a laser ray directed via a set of mobile mirrors, the movement of the ray reproducing an image.

The first approach involves an imager: a light source, an image-bearing support, for example a negative, and a focusing system.

Imager

The radiation system may comprise an imager or a mobile ray reproducing an image. The lighting system may comprise an addressable electronic matrix imager, such as, for example, an imager described in document No. FR 2 942 405.

An addressable matrix imager makes it possible to project a pixelated image, the resolution of which is, for example, greater than 10 by 10 pixels and preferentially greater than 10 by 100 pixels.

When the imager is an addressable electronic matrix imager, the image formed on the area to be treated is formed from pixels which are on or off, optionally each according to a predefined level of gray.

A computer can determine the digital image on the basis of which the electronic imager is controled, in particular the level of gray of each pixel, and also optionally the dominant wavelength of the light at the level of each pixel.

The addressable matrix imager can be produced on the basis of several technologies.

Use may be made of the technology termed DLP (Digital Light Proccessing) invented by the company Texas Instruments, which uses a DMD (Digital Micromirror Device) chip composed of thousands of micromirrors, the direction of which can be controled individually under the effect of an electric pulse, and which can possibly reflect, depending on their direction, an incident light beam in order to possibly send it back to the optical outlet of the imager. The image to be projected is formed on the matrix of mirrors.

The levels of gray of each pixel (for example 256 levels in number) may be controled by adjusting the cyclic ratio.

The irradiator may also use the technology termed LCD.

The irradiator may comprise at least one dichroic mirror.

The projection system may also be based on the technology termed LCOS, liquid crystal on silicon. LCD technology is said to be transmissive since the light passes through an LCD screen, whereas DLP technology is said to be reflective, since the light is reflected by the micromirrors of the DMD chip. In LCOS technology, the mirrors of the DMD chips are replaced with a reflective surface covered with a layer of liquid crystals, which can be switched between a passing state and a blocking state. By modulating the frequency of opening and closing of the liquid crystals, the level of gray of a pixel can be varied.

Generally, the image delivered by the addressable matrix imager comprises a matrix of pixels, the levels of gray of which are individually addressable, each level of gray being, for example, coded on at least 4 bits, better still 8 bits. The light associated with each pixel can also be the subject of coding, where appropriate.

The image to be projected can be supplied to the electronic imager in the form of a VGA, SVGA, composite, HDMI, SVIDEO, $YC_BC_R$ or optical video signal, amongst other standard signals, or in the form of a computer image or video file, for example .jpeg, .pdf, .ppt, etc. On these images, when they are not monochrome, a color which is predefined on the image in the file can control the level of UV or near UV, for example.

The electronic imager is advantageously constructed in such a way as to be able to change the nature of the light emitted without changing the image; for example, the pixels of the image keep their levels of gray and only the emission spectrum of the source used upstream changes. This may make it possible to visualize an image on the area to be treated and then to reveal it, simply by modifying the emission spectrum of the source.

Analysis of the Area to be Treated and Choice of the Image Projected

The treatment system may comprise a system for analyzing the areas to be treated. For example, the analysis system scans the skin and/or the lips and determines, by human or automatic intervention, the areas to be irradiated.

The treatment system can be configured for automatically detecting a skin defect on the area to be treated, and the imager can be controlled according to the nature of the defect detected.

The treatment system may have particular recognition functions, intended, for example, to recognize the defects, for example: wrinkles, cracks, stretchmarks, veins, recessed areas or bumps, such as scars, asymmetries.

The defects can be detected by image and/or relief analysis. The image analysis may be 3D image analysis. The treatment system may comprise means for acquisition of the 3D shape of the face or the part of the body to be treated.

The choice may, for example, be made according to a logic of re-establishment of symmetry for faces which have asymmetries and/or according to a logic of light and shadow, through which a face which is too angular can be made more round, or vice versa, or proportions which are not very esthetic or natural can be corrected.

The treatment system can be configured so as to scroll several pictorial models, in the form of simulations, in order to enable a person to select, among them, the model to be produced.

The treatment system can offer the possibility of rapidly trying all sorts of models, by projection directly onto the face. Thus, the person can see, in a real version, how suitable this or these model(s) is (are) for them.

The treatment system can be configured so as to take an image, for example using the abovementioned optical acquisition device, to optionally extract therefrom a part corresponding to the area to be treated, and to make it possible to correct, where appropriate, this image in order to improve the rendering thereof once projected.

The treatment system used is preferentially configured so as to enable the user, on the basis of an image projected onto the face or onto any other area to be treated, to correct the shape thereof, for example by enlarging or shrinking, in one or two dimensions. The modifications may also be more complex. Thus, it is possible, for example, to correct a part of the image, stretch a particular area, change the size of the features. In this, use may be made of the tools usually present in image producing and retouching software, such as Photoshop® for example. The image retouching can be carried out, where appropriate, by virtue of a return of information by the optical acquisition device, the computer being able to determine the rendering of the projected image and to automatically modify it until the desired result is achieved, during the execution of a software loop by the treatment system.

Other Means of Activation

The treatment assembly may comprise at least one source of another means of activation selected from a source of heat, of microwaves, of sound waves, a light source which does not facilitate crosslinking of the compound(s), Modeling Device The assembly for treating esthetic defects/imperfections of the skin and/or of the lips may comprise a system for applying a stress before or during the illumination.

A completely integrated system/device can be used.

Treatment Process

In another aspect of the invention, the subject thereof is a cosmetic process for treating the skin and/or the lips, comprising the following steps:

i. administration into or through the skin and/or the lips of a composition as previously defined, ii. illumination of the skin and/or the lips treated according to step i. in order to crosslink the composition.

As specified above, it is also possible to use a tracer (fluorescent group) in order to assist the practitioner in locating the composition once injected. In doing so, this helps to irradiate the entire area where the composition is located.

Preferably, the tracer changes appearance (changes color or becomes colorless) when the polymerization has taken place.

In one particular embodiment, the process comprises, after the step of injecting the composition, a step of modeling, for example by suction, smoothing, extension, traction or compression. This is a great advantage, since it allows modeling effects.

The modeling step may be prior to and/or simultaneously with the illumination.

During this step, the treatment area may be, at least partly, subjected to another energy action, such as the application of heat, microwaves, laser, or illumination at a wavelength which does not cause crosslinking of one of the compounds of the composition.

According to one embodiment, the injection step can be repeated on all or part of the surface to be treated. The repetition of the injections makes it possible to create a layering such that the composition of the invention is distributed homogeneously in the skin region to be treated.

A composition of the invention may be advantageously injected at the level of the wrinkles and fine lines.

There are several injection techniques. For example, in the case of an injection by mesotherapy, micropuncture (needle pricks close together) or multipoint (needle pricks at several points further apart) may be used.

The repeated injections can also be carried out point-by-point manually. The needle prick points can, for example, be spaced apart by a distance ranging from 5 mm to 1 cm.

According to one embodiment, a process of the invention can be carried out in several sessions several days apart, for example 1, 2, 3, 4, 5 or 6 days to a few weeks apart, for example 1, 2, 3 or 4 weeks apart.

According to one embodiment, the step(s) of administration by injection can advantageously be carried out by means of an injection gun, in particular a hydropneumatic-compression injection gun with a high injection frequency as previously defined.

The process may comprise a step of eliminating the part of the composition which has not crosslinked. For example, it is possible to pierce the skin and to suction the compound which has remained fluid.

It is possible, after illumination, to apply, topically or by injection, a third compound intended to react with the unreacted functions, so as to avoid subsequent photo-crosslinking. For example, a product which is a monomer of the same function is injected.

According to one particular embodiment, the skin regions advantageously treated by means of a process of the invention may be the skin of the face and neck, of the neckline, of the abdomen and of the legs.

The process may comprise a first illumination of a treatment area corresponding to only a part of the skin and/or of the lips having received the composition, which part it is desired to treat differently, in particular more strongly, and a second illumination on all of the skin and/or of the lips having received the composition.

According to the invention, the process for treating the esthetic defects/imperfections of the skin and/or the lips can comprise at least one step aimed at:

modeling the skin, the lips,
filling the wrinkles or furrows of the skin,
repairing the skin, for example the stretchmarks, the scars, in particular acne scars,
retightening the skin,
lifting parts of the body which have sagged,
increasing the volume of certain parts of the body, in particular of the face, especially the edge of the lips,
reinforcing the maintenance of implants, of fillers or of active compounds.

The present invention can be used for the treatment, prevention and/or reduction of the unsightly effects of aging of the skin and/or of the lips. For the purposes of the invention, the term "prevention" is intended to mean reducing the risk of ocurrence of a phenomenon. A subcutaneous layer intended for preventing slackening of the skin can, for example, be created.

The process in accordance with the present invention thus proves to be advantageous for treating aging of the skin and/or photo-aging of the skin.

It also makes it possible to prevent and/or treat signs of aging of the skin or of photo-aging of the skin, selected from wrinkled skin, skin exhibiting a modification of its viscoelastic or biomechanical properties, skin exhibiting a modification in the cohesion of its tissues, thinned skin, and skin exhibiting a modification of its surface appearance and/or texture, in a device for intradermal and/or a intraepi-dermal subcutaneous administration.

The present invention may, for example, be used in prevention of slackening of the skin.

The skin and/or the lips can be pretreated with a different composition, not covered by the invention, before administration of the composition comprising the group intended for photo-crosslinking.

The skin and/or the lips can be treated with a different composition, not covered by the invention, after administration of the composition comprising the group intended for photo-crosslinking and before illumination.

The skin and/or the lips can be treated with a different composition, not covered by the invention, after illumination and before rinsing.

After illumination and after rinsing, the skin and/or the lips can, in another variant, be treated with a different composition, not covered by the invention.

For example, the skin and/or the lips can be treated with reactive or nonreactive agents which improve the adhesion of the material or protective agents, in particular protective against UV light, or else agents which delay the wear of the material.

Figure 1B:
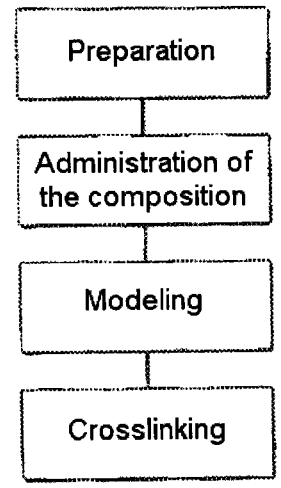
Figure 2A:
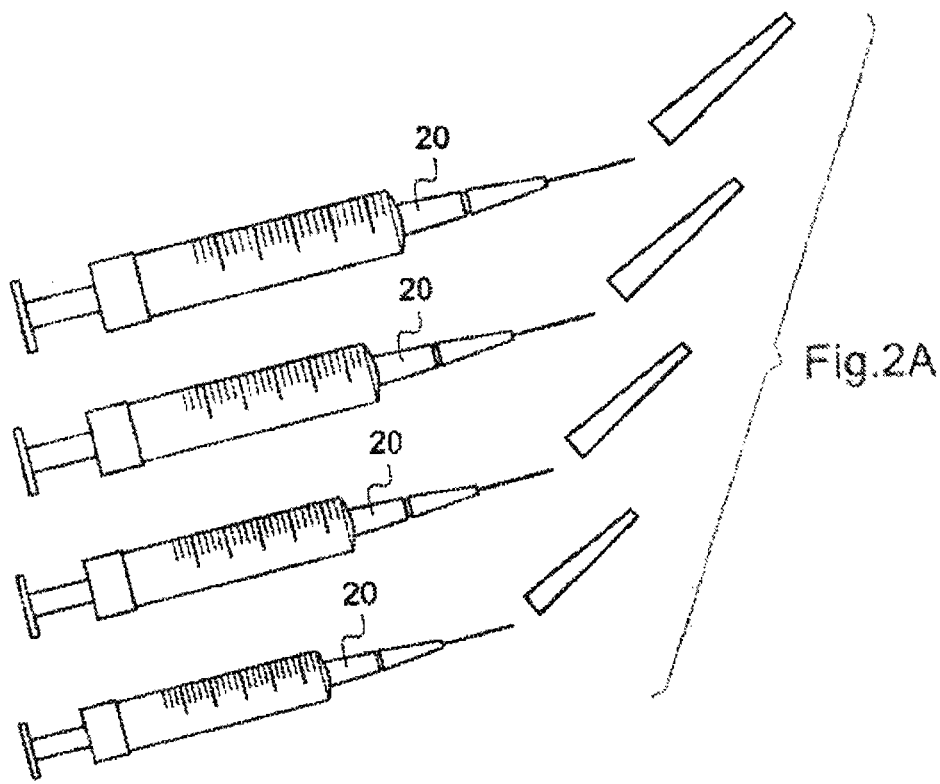
Figure 2B:
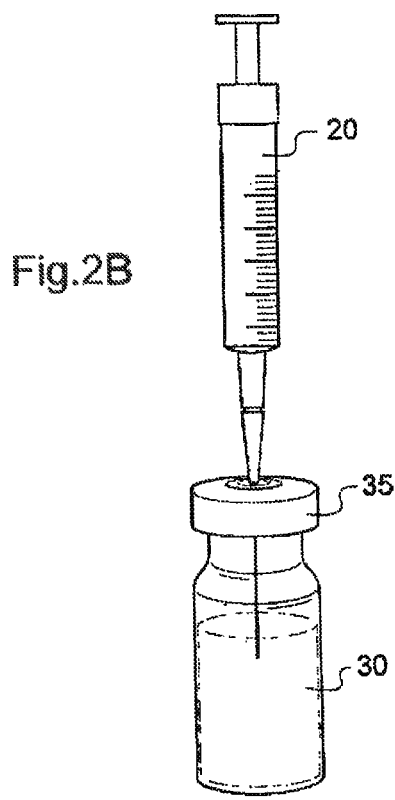
Figure 2C:
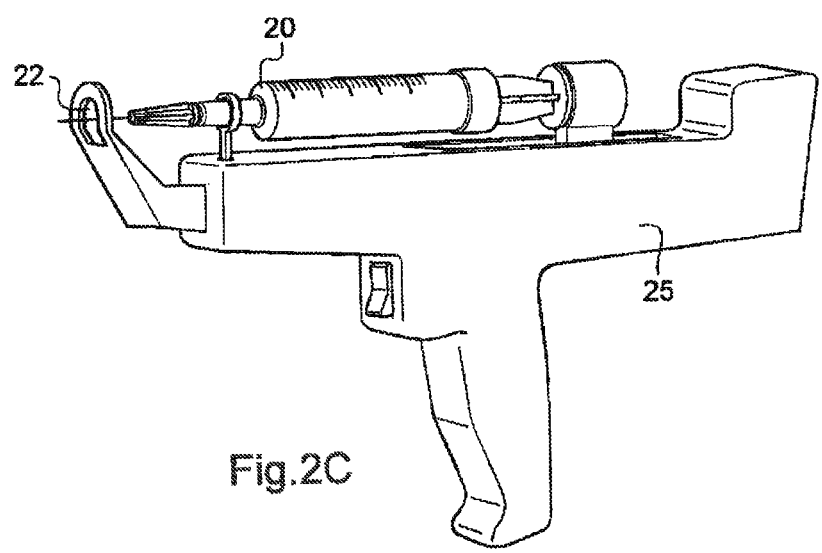

The invention may be better understood from reading the following detailed description of nonlimiting implementation examples thereof and from examining the appended drawing, in which:

FIGS. 1A and 1B represent diagrammatically two methods of using a treatment system according to the invention, FIGS. 2A to 2C represent injection devices of a treatment system according to the invention, FIG. 3 represents diagrammatically a treatment assembly, and FIGS. 4a and 4b represent a modeling system.

The preparation step shown in FIGS. 1A and 1B corresponds to preparing, on the one hand, the material for the injection, which depends on the technique selected, and, on the other hand, the composition to be injected.

The composition may be prepared in situ, or may be prepackaged, in particular in sterile packaging.

The packaging is suitable for the storage of at least one dose of the composition, where appropriate for the mixture thereof with a physiologically acceptable liquid medium, in a sterile environment.

The packaging may be arranged so as to allow, moreover, the sampling of said composition in the form of a solution or dispersion Thus, according to a first embodiment, said packaging is scored so as to allow said composition to be sampled.

For example, it may be in the form of a single-dose capsule or vial, which has a scored end.

According to a second embodiment, said packaging has a seal which allows hermetic closing during storage and which can be pierced by a needle at the time of use.

According to one embodiment variant, said composition is formulated in the form of a dispersion or of a solution within the packaging.

According to another variant, said composition is present in powder form.

In such a variant, said packaging is suitable for the introduction of a sterile, fluid, physiologically acceptable medium in order to obtain a solution and/or dispersion of said composition under sterile conditions.

Such packaging may also be two-compartment packaging, one of the compartment s being dedicated to the storage of said composition in the powder form and the other to the storage of the physiologically acceptable liquid medium which must be combined therewith. These two compartments are advantageously separated by a blocking means configured so as to be moved and to then allow the content of the two compartments to mix.

Such a device is advantageously disposable.

FIG. 2A represents several syringes 20, prefilled with a dose of composition. The doses correspond, for example, respectively to 1 ml, 1 ml, 1 ml and 1 ml of composition.

In the variant of FIG. 2B, the syringe 20 is not prefilled and the composition is packaged in a sterile bottle 30. In the example shown, the bottle is hermetically closed with a closing member 35 made of a flexible material, able to be pierced by the needle of the syringe 20. Other modes of closure can be envisioned.

FIG. 2C represents a perspective view of a gun 25 used for an administration of the composition by mesotherapy. The syringe 20 and the sight 22 are preferably disposable.

The examples represented are not limiting. Those skilled in the art can select any known intradermal injection or application technique.

After administration of the composition, the area to be treated, for example the face as shown in FIG. 3, is lit so as to crosslink the compound.

In the example shown, the crosslinking is produced by an artificial light source; in another variant, the crosslinking can be carried out in daylight.

The treatment system of FIG. 3 optionally comprises an electronic imager 4 produced according to DLP technology, using a DMD chip referenced 111. The latter can be attached to a platform 112 which can comprise, moreover, a processor 113 for controlling the chip, and also, optionally, a memory 114. In the example shown, the chip is represented on the same platform as the processor 113 and the memory 114, but said processor and said memory can be arranged differently.

The imager 4 represented in FIG. 3 receives light from a source 2 which may be a source that can emit both in the UV range and/or in the visible range or a source that can emit selectively in the visible range or in the UV range.

The source 2 may be a halogen lamp which emits in the UV and visible spectra, a discharge lamp or one or more LEDs capable of emitting, for example, in the UV range or in white light or light in a given color.

The imager 4 may comprise, as shown, optics 118, 119 and 120 respectively for condensing the light, focusing it on the DMD chip and ensuring focusing on the area to be treated.

When the source 2 has an emission spectrum both in the UV range and in the visible range, the imager 4 may comprise, as shown, a filter wheel 130, which intercepts the light beam, for example, between the condensing optic 118 and the focusing optic 119. Depending on the position of the filter wheel 130, the chip receives UV light or visible light, which is then directed to the optical outlet. It is thus possible to form, on the area to be treated, an image selectively in visible light and/or in the UV range.

In one variant which is not represented, the irradiator uses several DMD chips attached to a prism.

The arrangement shown in FIG. 3 can be used with the DMD chips replaced with LCOS chips.

Once the composition has been injected, the method shown in FIG. 1B also comprises a modeling step intended to force the material to give the skin a better conformation.

This step can be carried out by several means, optionally combined, in particular by suction, smoothing, extension, energy actions such as radiation by microwave or laser.

The modeling can be carried out in dim light, or even in the dark, before the beginning of the crosslinking phase.

In another variant, the modeling can be carried out simultaneously with the crosslinking, at least partly, for example can begin prior to and continue during the crosslinking step.

In one variant, the modeling is carried out by massaging the treatment area in order to preform the composition before crosslinking. The massaging can be done manually and/or using a massaging member.

FIGS. 4A and 4B show a system 40 for applying a stress, placed directly on the skin at the level of a wrinkle or of a furrow, as shown in FIG. 4A. The system generates forces which have the effect of retightening the skin.

The process shown in FIG. 1B also optionally comprises a step of eliminating the part of the composition which has not crosslinked.

Other features and advantages of the invention will emerge from the examples that follow, which are given as nonlimiting illustrations.

In the text hereinbelow, the proportions are given as weight percentages, unless otherwise indicated.

The expression "comprising a" is synonymous with "comprising at least one", and "between" should be understood to mean limits inclusive.

The examples that follow are given as nonlimiting illustrations of the present invention.

The invention is not limited to the devices shown.

EXAMPLE 1

Synthesis of Xanthan Gum Grafted with Stilbazolium Groups

Deacetylated xanthan gum is prepared by dissolving 0.2% by weight of xanthan gum (Rhodicare® XC from Rhodia) in water and by adding 0.025 mol of potassium hydroxide and 0.1% by weight of potassium chloride for 2 h 30 at ambient temperature, under a nitrogen atmosphere.

The alkaline solution is then neutralized with 0.05 mol of hydrochloric acid in order to adjust the pH to 6.5.

The solution is then dialyzed with distilled water using dialysis tubing (Snakeskin™ Pleated Dialysis Tubing, Pierce, Rockford, Ill., U.S.A.), and the deacetylated xanthan is recovered by lyophilization.

The deacetylated xanthan gum is redissolved in 20 ml of water.

0.2 g of concentrated phosphoric acid and 0.1 g of chloride compound (1) of formula:

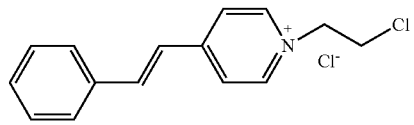

are dissolved in 1 ml of water and are added thereto.

The mixture is kept stirring at ambient temperature overnight.

The mixture is then precipitated with acetone and washed with methanol containing aqueous ammonia.

Synthesis of the Chloride Compound (1) of Formula:

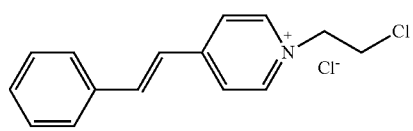

A mixture of 4-styrylpyridine (2.3 g, 12.5 mmol) (J. L. R. Williams, R. E. Adel, J. M. Carlson, G. A. Reynolds, D. G. Borden, J. A. Ford, *J. Org. Chem.*, 1963, 28, 387) and 1,2-dichloroethane (5 g, 50 mmol) was heated in the dark for 4 hours at 150° C. using an oil bath. The mixture was then dissolved by heating it in 30 ml of anhydrous ethanol and then cooled to 5° C.

The precipitate obtained was filtered off, washed with chloroform and air-dried.

EXAMPLE 2

Synthesis of Starch Grafted with Stilbazolium Groups 20 g of sodium sulfate and 1.5 g of sodium hydroxide are dissolved in 75 ml of water and heated to 40° C.

50 g of corn starch (Farma® CS 3757 sold by Corn products international) are rapidly added with stirring.

4 g of chloride compound (1) are added while maintaining the pH above 11.6. The mixture is stirred for 24 hours at 40° C. The reaction is then cooled to ambient temperature and the pH is adjusted to 7 with hydrochloric acid.

The modified starch is then filtered and the filtrate is washed with water and air-dried.

EXAMPLE 3

Synthesis of Alginate Grafted with Stilbazolium Groups 1 g of sodium alginate (Kelcosol NF sold by FMC corporation) is dissolved in 100 ml of water. The pH of the solution is then adjusted to 11.6 with sodium hydroxide.

0.1 g of chloride compound (1) dissolved in 1 ml of water is added to the reaction medium while maintaining the pH at 11.6. The mixture is stirred for 24 hours at 40° C. and then cooled to ambient temperature and the pH is adjusted to 7 with hydrochloric acid.

The mixture is precipitated with acetone, and the precipitate is washed with methanol and then air-dried.

EXAMPLE 4

Synthesis of Chitosan Grafted with Stilbazolium Groups

The grafted chitosan is obtained in the same way as the alginate previously described, using chitosan (Chitoclear SC342 from Primex).

EXAMPLE 5

The following composition is prepared and is then packaged in a bottle under a sterile atmosphere.

| Compounds | Amount (% by weight) |
| --- | --- |
| Polyvinyl alcohol with pendent N-methylstyrylpyridium groups, in methyl sulfate salt form, sold by the company Polymer Science under the name PS22570 | 6.9 |
| Distilled water | 83.1 |
| Rhamnose | 5 |
| Glycerol | 5 |

This injectable composition is used for a treatment of wrinkled epidermis via the technique of injection with a syringe to a depth of 0.5 mm below the surface area.

The area to be treated is then lit by an imager with a first dominant wavelength in the visible range of 8.5 mW/cm² for 120 s, i.e. approximately 1 J/cm².

The whole of the area having received the composition is then lit by an imager with a second dominant wavelength in the UVA range of 12 mW/cm² for 120 s.

The excess composition is eliminated by dabbing. After photo-polymerization of the injected polymer, a reduction in the wrinkles at the surface of the skin is observed.

Another embodiment is described hereinafter.

The injectable composition is used for a treatment of the epidermis via the technique of injection with a syringe to a depth of 0.3 mm below the surface area of a wrinkle, and the injection is carried out little by little while withdrawing the syringe.

The area to be treated (0.2 cm by 2 cm) is then lit by an imager with a 405 nm Led Laser pointer of 15 mW (from the company Global Laser) which is defocused so as to cover a surface of 0.4×0.4 cm (i.e. 0.16 cm²).

A device keeps the imager away from the skin.

A scan is performed (0.1 cm/s) in order to treat the area over the 2 cm of length of the wrinkle.

Thus, a surface of 0.4 cm by 2 cm, i.e. 0.8 cm², is treated.

The treatment lasts for 200 s, i.e. 4 J/cm².

EXAMPLE 6

The following composition is prepared and is then packaged in a bottle under a sterile atmosphere:

| Compounds | Amount (%) |
|---|---|
| Xanthan gum grafted with stilbazolium groups (example 1) | 5 |
| Distilled water | 90 |
| Glycerol | 5 |

The resulting composition is used for a treatment of wrinkled epidermis in accordance with that described in example 5.

EXAMPLE 7

The following composition is prepared and is then packaged in a bottle under a sterile atmosphere:

| Compounds | Amount (%) |
|---|---|
| Starch grafted with stilbazolium groups (example 2) | 5 |
| Distilled water | 90 |
| Glycerol | 5 |

The resulting composition is used for a treatment of wrinkled epidermis in accordance with that described in example 5.

EXAMPLE 8

The following composition is prepared and is then packaged in a bottle under a sterile atmosphere:

| Compounds | Amount (%) |
|---|---|
| Alginate grafted with stilbazolium groups (example 3) | 5 |
| Distilled water | 90 |
| Glycerol | 5 |

The resulting composition is used for a treatment of wrinkled epidermis in accordance with that described in example 5.

EXAMPLE 9

The following composition is prepared and is then packaged in a bottle under a sterile atmosphere:

| Compounds | Amount (%) |
|---|---|
| Chitosan grafted with stilbazolium groups (example 4) | 5 |
| Distilled water | 90 |
| Glycerol | 5 |

The resulting composition is used for a treatment of wrinkled epidermis in accordance with that described in example 5.

The invention claimed is:

1. A sterile liquid composition to inject into or through the skin and/or the lips suitable for filling wrinkles, comprising, in a physiologically acceptable medium, an antiwrinkle active agent, a photo-crosslinkable compound, wherein the photo-crosslinkable compound is a polyvinyl alcohol partly functionalized with one or more hydroxyl groups and one or more groups of formula (III):

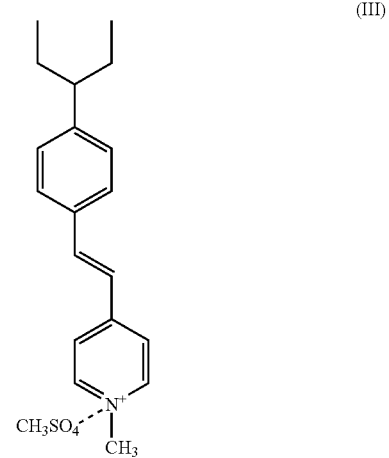

(III)

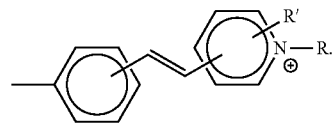

2. The composition of claim 1, comprising no photoinitiator, comprising no chemical initiator, or comprising neither a photoinitiator nor a chemical initiator.

3. The composition of claim 1, comprising 2 vol % or more of the photo-crosslinkable compound, based on a total volume of the composition.

4. The composition of claim 1, further comprising an optical tracer or a fluorescent compound.

* * * * *